United States Patent [19]

Walser

[11] Patent Number: 5,175,144
[45] Date of Patent: Dec. 29, 1992

[54] METHOD OF RETARDING THE PROGRESSION OF CHRONIC RENAL FAILURE

[75] Inventor: Mackenzie Walser, Ruxton, Md.

[73] Assignee: The Johns Hopkins University, Baltimore, Md.

[21] Appl. No.: 277,161

[22] Filed: Nov. 29, 1988

[51] Int. Cl.⁵ .................. A61K 37/00; A61K 31/56; A61K 21/495; A61K 31/50; A61K 31/44; A61K 31/445

[52] U.S. Cl. .................................. 514/2; 514/11; 514/179; 514/252; 514/282; 514/289; 514/327

[58] Field of Search .............. 514/179, 2, 11, 252, 514/282, 289, 327

[56] References Cited

U.S. PATENT DOCUMENTS 3,714,159  1/1973  Janssen et al. .............. 424/601
4,320,146  3/1982  Walser ......................... 424/601

OTHER PUBLICATIONS

The Merck Manual (14th edition, 1982) pp. 2388-2389.
Avery's Drug Treatment, 3rd edition (1987) pp. 897-898.
W. E. Mitch, et al., "The Effect of Keto Acid-Acid Supplement to Restricted Diet on the Progression of Chronic Renal Failure", *The New England Journal of Medicine*, 311:623-629 (Sep. 6), 1984.
J. Burns, et al., "Comparison of the effects of keto acid analogues and essential amino acids on nitrogen homeostasis in uremic patients on moderately protein-restricted diets", *The American Journal of Clinical Nutrition* 31: Oct. 1978, pp. 1767-1775.
M. Walser, et al., "Progression of chronic renal failure in patients given ketoacids following amino acids", *Kidney International*, vol. 32 (1987), pp. 123-128.
N. Gretz, et al., "Low-proteindiet supplemented by keto acids in chronic renal failure: A prospective controlled study", *Kidney International*, vol. 24, Suppl. 16 (1983), pp. S-263-S-267.
G. Barsotti, et al., "Effects on Renal Function of a Low-Nitrogen Diet Supplemented with Essential Amino Acids and Ketoanalogues and of Hemodialysis and Free Protein Supply in Patients with Chronic Renal Failure", *Nephron* 27:113-117 (1981).
T. Taylor, et al., "B-Endorphin Suppresses Adrenocorticotropin and Cortisol Levels in Normal Human Subjects", *Journal of Clinical Endocripology and Metabolism*, vol. 57, No. 3, pp. 592-596 (1983).
B. Ambrosi, et al., "Loperamide, an Opiate Analogue, Inhibits Plasma Acth Levels in Patients with Addison'-Disease", *Clinical endocrinology*, 24, pp. 483-489 (1986).
G. Teutsch, et al., "17a-Alkynyl-11b,17-Dihydroxyandrostane Derivatives: A New Class of Potent Glucocortincoids.", *Steroids*, vol. 38, No. 6, pp. 651-665 (1981).
M. Moguilewsky, et al., "RU 38486: Potent Antiglucocorticoid Activity Correlated with Strong Binding to the Cytosolic Glucocorticoid Receptor Followed by an Impaired Activation", *S. Steroid Biochem*, vol. 20, No. 1, pp. 271-276 (1984).
Roland M. Schaefer, et al., "Evidence for Reduced Catabolism by the Antiglucocorticoid RU 38486 in Acutely Uremic Rats", *Am. J. Nephrol*, 7, pp. 127-131 (1987).
Xavier Bertagna, et al., "The New Steroid Analog RU 486 Inhibits Glucocorticoid Action in Man", *Journal of Clinical Endocrinology and Metabolism*, vol. 59, No. 1, pp. 25-28 (1984).

(List continued on next page.)

Primary Examiner—Frederick E. Waddell
Assistant Examiner—Raymond J. Henley, III
Attorney, Agent, or Firm—Panitch Schwarze Jacobs & Nadel

[57] ABSTRACT

Progression of chronic renal failure can be retarded (slowed or arrested) by administering to humans suffering from such disorder an agent which suppresses the production of glucocorticoids in the human. The agents may be administered alone or in combination with a protein restricted and/or phosphorus restricted diet. Examples of suitable agents which either suppress production of glucocorticoids or block binding to their receptors include sodium valproate, enkephalins, opioids, clonidine, ketoconazole, oxytocin, and mifepristone.

10 Claims, 1 Drawing Sheet

OTHER PUBLICATIONS

J. J. Legros, et al., "Confirmation of the Inhibitory Influence of Exogenous Oxytocin on Cortisol and ACTH in Man: Evidence of Reproducibility", *Acta Endocrinologica*, 114: pp. 345-349 (1987).

Farwell, et al., "Total Suppression of Cortisol Excretion by Ketoconazole in the Therapy of the Ectopic Adrenocorticotropic Hormone Syndrome", *The American Journal of Medicine*, vol. 84 (Jun. 1988), pp. 1063-1066.

Stowinski-Srzednicka, et al., "Effect of Clonidine on Beta-Endorphin, ACTH and Cortisol Secretion in Essential Hypertension and Obesity," *Eur. J. Clin. Pharmacol* (1988) 35:115-121.

Lechin, et al., "Role of Stress in the Exacerbation of Chronic Illness: Effects of Clonidine Administration on Blood Pressure and Plasma Norepinephrine, Cortisol, Growth Hormone and Prolactin Concentrations,"*Psychoneuroendocrinology*, vol. 12, No. 2 pp. 117-129 (1987).

Stubbs, et al., "Hormonal and Metabolic Responses to an Enkephaline Analogue in Normal Man," *The Lancet*, Dec. 9, 1978, pp. 1225-1227.

Pende, et al., "Evaluation of the Effects Induced by Four Opiate Drugs, with Different Affinities to Opioid Receptor Subtypes, on Anterior Pituitary LH, TSH, PRL and GH Secretion and on Cortisol Secretion Normal Men,"*Biomedicine & Pharmacotherapy*, 1986, 40, 178-182.

Aggernaes, et al., "The Effect of Sodium Valproate on Serum Cortisol Levels in Healthy Subjects and Depressed Patients," *Acta Psychiatr. Scand.* 1988:77:170-174.

Nieman, et al. "Clinical Applications of the Glucocorticoid and Progestin Atnagonist RU 486," appearing in *Receptor Mediated Antisteroid Action*/Editor M. K. Agarwal (1987).

Gagne, et al., "RU38486: A Potent Antiglucocorticoid in Vitro and In Vivo," *J. Steroid Biochem*, vol. 23, No. 3, pp. 247-251 (1985).

Mitch et al., "Long-Term Effects of a New Ketoacid-Amino Acid Supplement in Patients with Chronoc Renal Failure," *Kidney International*, 22:48-53 (1982).

METHOD OF RETARDING THE PROGRESSION OF CHRONIC RENAL FAILURE

BACKGROUND OF THE INVENTION

Since the first anecdotal evidence that nutritional therapy may slow the progression of chronic renal failure (see Walser M., "Ketoacids in the Treatment of Uremia," *Clinical Nephrology*, 3:180–7 (1975)), there has been growing interest in two possibilities: (1) that a common mechanism causes progression of many types of chronic renal failure, and (2) that this process can be slowed or arrested by diet or drugs.

Many mechanisms have been postulated, based on experiments in animals and/or clinical observations. Factors proposed to contribute to progression include arterial pressure, and more specifically, glomerular capillary pressure which is reduced by angiotensin-converting enzyme inhibitors; serum calcium times phosphorus product; urinary phosphorus excretion; protein intake itself; hyperuricemia; hypertriglyceridemia; hypercholesterolemia; and hyperoxalemia. As yet, no studies have examined the influence of such factors acting in concert on progression of chronic renal failure.

Ketoacid mixtures, administered in conjunction with a low protein, low phosphate diet, have been reported to slow progression in several studies, see Mitch. W. E., et al., "The Effect of a Keto Acid-Amino Acid Supplement to a Restricted Diet on the Progression of Chronic Renal Failure," *New England Journal of Medicine*, 311:623–9 (1984); Gretz, N., et al., "Low-Protein Diet Supplemented by Ketoacids in Chronic Renal Failure: A Prospective Study," *Kidney International*, 24, Suppl. 16:S263–7 (1983); and Barsotti, G., et al., "Effects on Renal Function of a Low-Nitrogen Diet Supplemented with Essential Amino Acids and Keto Analogs and of Hemodialysis and Free Protein Supply in Patients with Chronic Renal Failure," *Nephron*, 27:113–7 (1981), but see Burns, J., et al., "Comparison of the Effects of Ketoacid Analogs and Essential Amino Acids on Nitrogen Homeostasis in Uremic Patients on Moderately Protein-Restricted Diets," *American Journal of Clinical Nutrition*, 31:1767–1775 (1978).

However, in most of these reports, no attempt was made to differentiate between the effects of the diet and the ketoacids. More recently, it has been reported that some patients progressing on this diet supplemented with essential amino acids exhibit slowed or arrested progression when changed to ketoacids, suggesting a specific effect of ketoacids on progression, see Walser, M., et al., "Progression of Renal Failure in Patients Given Ketoacids Following Amino Acids," *Kidney International*, 32:123–6 (1987).

BRIEF SUMMARY OF THE INVENTION

According to the present invention, it has now been discovered that the progression of chronic renal failure in humans may be retarded by administering to humans suffering from such disorders an effective amount of an agent which suppresses the endogenous production of glucocorticoids. Preferably, such agents are administered while the patient is on a protein and phosphorus-restricted diet, since these restrictions also suppress endogenous glucocorticoid production. The restrictions are to preferably less than about 0.6 grams of protein daily per kilogram of ideal body weight and less than about 10 milligrams phosphorus daily per kilogram of ideal body weight.

Agents believed to be useful in the present invention include drugs which reduce glucocorticoid production directly or reduce or block receptor binding of the glucocorticoids. Examples of such agents include opioids, such as morphine, pentazocine, nalorphine, buprenorphine, and loperamide; enkephalins and their analogs such as DAMME; sodium valproate; clonidine; ketoconazole; oxytocin; and mifepristone.

While the mechanism was not previously known, the use of ketoacid therapy in retarding the progression of chronic renal failure was previously known. Accordingly, the use of ketoacid therapy is excluded from the claimed invention.

DETAILED DESCRIPTION OF THE PREFERRED EMBODIMENTS

Figure 1:
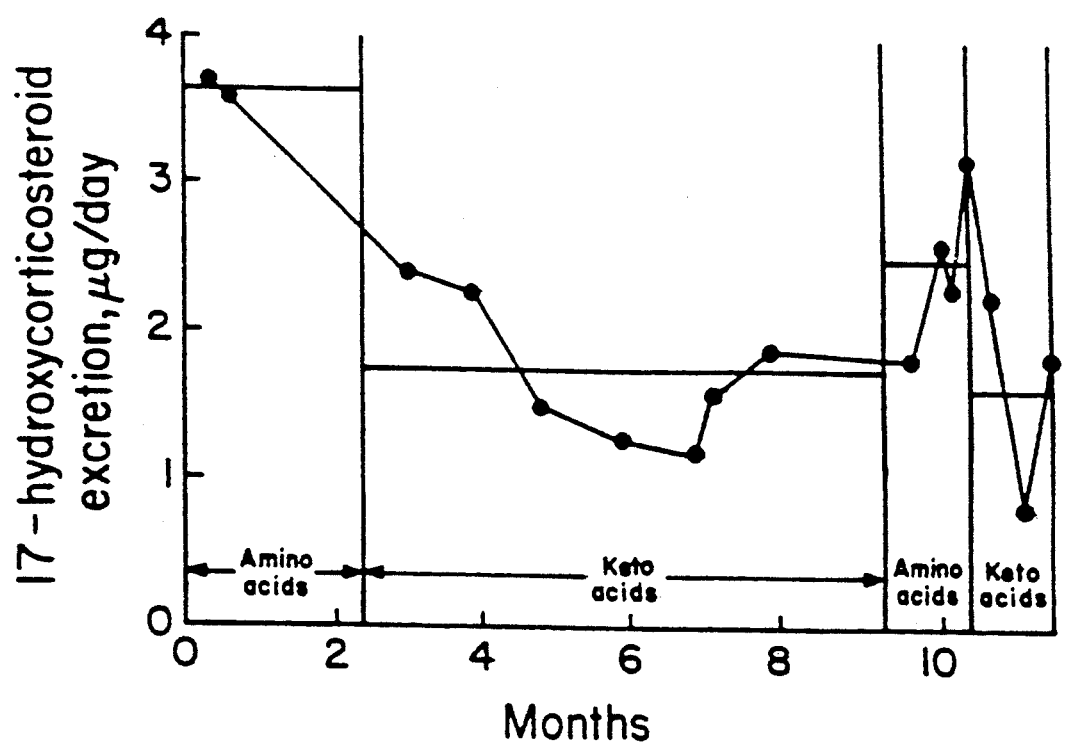

Glucocorticoids are corticosteroids predominantly affecting carbohydrate metabolism. Endogenous glucocorticoids influence fat and protein metabolism and have many other activities, such as affecting muscle tone and the excitation of nerve tissue and the microcirculation. In humans, the most important glucocorticoid is cortisol (hydrocortisone).

Glucocorticoids play a role in the regulation of protein turnover. They are often used therapeutically in chronic renal disease. Surprisingly, it has been found according to the present invention that suppression of the endogenous production of glucocorticoids or blocking of their binding to receptors slows or arrests the progression of chronic renal failure. Thus, it is believed that the beneficial immunological effects of glucocorticoids previously administered at high dosage obscures a deleterious effect on progression within the physiological range of hormone production, mediated perhaps by an effect on renal protein turnover.

While applicant does not wish to be bound by any particular theory, the above may explain why ketoacid therapy with branched-chain ketoacids, especially alpha-ketoisocaproate, exerts protein-sparing effects, as well as slowing the progression of chronic renal failure as reported above. That is, these two different effects of ketoacids might be related by the common mechanism of suppressing glucocorticoid production.

Aside from ketoacid therapy which has previously been reported to retard the progression of chronic renal failure, the following agents which are known to suppress glucocorticoid production or block their receptor binding in humans would appear to be useful according to the present invention in retarding the progression of chronic renal failure:

(1) Sodium valproate: This is an anticonvulsant, widely used, but not without serious side effects and toxicity. It has recently been shown to reduce serum cortisol levels by more than fifty percent within a few hours in normal subjects. Aggernaes, H. et al., "The Effect of Sodium Valproate on Serum Cortisol Levels in Healthy Subjects and Depressed Patients," *Acta Psychiatr. Scand.*, 77:170–174 (1988).

(2) Enkephalins: These pentapeptides and their synthetic analogs, notably "DAMME" ([D-ala$^2$, MePhe$^4$, Met(O)-ol] enkephalin), reduce cortisol levels acutely in man. Stubbs, W. A., et al., "Hormonal and Metabolic Responses to an Enkephalin Analog in Normal Man", *The Lancet*, 1978:1225–1227 (Dec. 9, 1978); and Taylor, T., "Beta-Endorphin Suppresses Adrenocorticotropin and Cortisol Levels in Normal Human Subjects," *Jour-* nal of Clinical Endocrinology and Metabolism. 57:592–596 (1983).

(3) Opioids: Alkaloids like morphine also interact with the same or similar receptors as enkephalins. Opioids shown to decrease cortisol levels in man include morphine, pentazocine, nalorphine and buprenorphine. Pende, A., et al., "Evaluation of the Effects Induced by Four Opiate Drugs, with Different Affinity to Opioid Receptor Subtypes, on Interior Pituitary LH, TSH, PRL and GH Secretion and on Cortisol Secretion in Normal Man," *Biomed Pharmacother*, 40:178–82 (1986). Chronic administration of these may not be practical owing to side effects and/or addictive properties. However, loperamide, commercially available under the trademark "IMODIUM" from Janssen Pharmaceutica, N. V., is not addictive, but does suppress adrenocorticotrophic hormone production. See Ambrosi, B., et al., "Loperamide, an Opiate Analog, Inhibits Plasma ACTH Levels in Patients with Addison's Disease," *Clinical Endocrinology*, 24:483–489 (1986). Loperamine and similar butyramides are described in U.S. Pat. No. 3,714,159 of Janssen, et al.

(4) Clonidine: This widely used antihypertensive drug has recently been shown to lower cortisol levels in man. See Slowinska-Srzednicka, J., et al., "Effect of Clonidine on Beta-Endorphin, ACTH and Cortisol Secretion in Essential Hypertension and Obesity," *European Journal of Clinical Pharmacology*, 35:115–121 (1988); and Lechin, F., et al. "Role of Stress in the Exacerbation of Chronic Illness: Effects of Clonidine Administration on Blood Pressure and Plasma Norepinephrine, Cortisol, Growth Hormone and Prolactin Concentrations," *Psychoneuroendocrinology*, 12:117–129 (1987). Clonidine is already commonly used to treat hypertension in patients with chronic renal failure.

(5) Ketoconazole: This is an antifungal agent found to inhibit adrenocortical glucocorticoid production profoundly or even completely. Farwell, A. P., et al., "Total Suppression of Cortisol Excretion by Ketoconazole in the Therapy of the Ectopic Adrenocorticotropic Hormone Syndrome," *The American Journal of Medicine*, 84:1063–1066 (1988). However, ketoconazole is quite toxic.

(6) Oxytocin: Intravenous infusion of this hormone (widely used to induce labor) lowers cortisol levels in normal men. Legros, J. J., et al. "Confirmation of the Inhibitory Influence of Exogenous Oxytocin on Cortisol and ACTH in Man: Evidence of Reproducability," *ACTA Endocrinologica*, 114:345–349 (1987). Oxytocin can be given as an intranasal spray, and side effects are minor.

(7) Mifepristone: Also known as RU486 or RU38486, available from Roussel-Uclaf. This new hormone analog blocks glucocorticoid receptors and has been used to treat hyperadrenocorticism (Cushing's syndrome). Bertagna, X., et al., "The New Steroid Analog RU486 Inhibits Glucocorticoid Action in Man," *Journal of Clinical Endocrinology and Metabolism*, 59:25–28 (1984); Moguilewsky, M., et al., "RU38486: Potent Antiglucocorticoid Activity Correlated with Strong Binding to the Cytosolic Glucocorticoid Receptor Followed by Impaired Activation," *Journal of Steroid Biochemistry*, 20:271–6 (1984); Gagne, D., et al., "RU38486: A Potent Antiglucocorticoid In Vitro and In Vivo," *Journal of Steroid Biochemistry*, 23:247–251 (1985); and Teutsch, G., et al., "17 Alpha-Alkynyl-11 Beta, 17-Dihydroxyandrostane Derivatives: A New Class of Potent Glucocorticoids," *Steroids*, 38:651–665 (1981).

Mifepristone also reduces protein catabolism in acutely uremic rats. Schaefer, R. M., et al., "Evidence for Reduced Catabolism by the Antiglucocorticoid RU38486 in Acutely Uremic Rats," *American Journal of Nephrology*, 7:127–131 (1987). Single doses induce abortion, and chronic use induces a state of hypoadrenocorticism, but the problem is how to evaluate to glucocorticoid function when the receptors are blocked. Nieman, L. K., et al., "Clinical Applications of the Glucocorticoid and Progestin Antagonist RU486," Agarwal, M. K., editor, *Receptor Mediated Antisteroid Action*, de Gruyter, Berlin, New York (1987).

In order to demonstrate the effect of agents which suppress endogenous glucocorticoid production on the progression of chronic renal failure, a clinical study was run as described below, in which ketoacid therapy was used to slow or arrest the progression of chronic renal failure from a number of different sources. The clinical tests demonstrate that progression of chronic renal failure correlates well with the 24 hour urinary excretion rate of 17-hydroxycorticosteroids which is a measure of endogenous glucocorticoid production.

Clinical Test Methods

Multiple regression analysis of the factors determining progression rate was performed, based on longitudinal observations during 35 treatment periods lasting an average of 15 months, in 27 patients (17 males and 10 females) with chronic renal failure. Age varied from 23 to 78 years (mean 51 years). Diagnoses were: diabetic nephropathy, 6; glomerulonephritis, 10; interstitial nephritis, 4; polycystic kidney disease, 4; unknown, 3. Patients with IgA nephropathy were excluded because of the variable course of this disorder. Four patients were treated by mild protein restriction alone. The other 23 were prescribed a diet containing 0.3 gm per kg ideal body weight of protein and 7–9 mg per kg ideal body weight of phosphorus, supplemented with vitamins. However, 24-hour urinary urea N analyses showed that compliance was poor and protein consumption was in fact higher, averaging about 0.56 gm per kg.

In 16 studies, subjects received a mixture of ketoacids and amino acids in a dose of 18 gm per day as follows:

| Compound | Millimoles/Day |
| --- | --- |
| L-tyrosine | 20 |
| L-threonine | 15 |
| L-ornithine alpha-ketoisovalerate | 7 |
| L-ornithine alpha-ketoisocaproate | 7 |
| L-ornithine R,S-alpha-keto-beta-methylvalerate | 7 |
| L-lysine alpha-ketoisovalerate | 7 |
| L-lysine R,S-alpha-keto-beta-methylvalerate | 7 |
| L-histidine alpha-ketoisocaproate | 4 |
| Calcium D,L-alpha-hydroxy-gamma-methylbutyrate | 2 |

In the remaining 15 studies, patients received a mixture of essential amino acids in a dose of 10 gm per day. Eight patients received first amino acids and then ketoacids. All were seen monthly or bimonthly. Blood pressure was measured at each visit in the sitting posture by a single observer, and averaged over the entire study. All but 4 patients received anti-hypertensive drugs, including enalapril in 5 cases. Diuretics were required in all but 6, sodium polystyrene sulfonate in 5, NaHCO$_3$ in 8, and aluminum-containing antacids in 3. All received CaCO$_3$, 2-3 gm per day. Twenty-four hour urine samples were obtained without a preservative, and were kept in a refrigerator during and after collection.

Fasting serum and 24-hour urine chemical values were measured in the Johns Hopkins Hospital Chemistry Laboratory. 17-hydroxycorticosteroid excretion (17OHCS) was measured in the Pediatric Endocrine Laboratory, using the Silber-Porter method. Glomerular filtration rate (GFR) was measured bimonthly as the urinary clearance of intravenously injected $^{99m}$Tc-DTPA (100uCi), subcutaneously injected $^{125}$I-iothalamate (35uCi), or both (in which case the two clearances were averaged). Three collection periods were averaged. Correction for body weight or surface area was not made. Progression was calculated as the linear regression of GFR on time in months. Pre-treatment values were not employed, in order to exclude bias introduced by a possible acute disease in GFR in response to reduction of protein intake. The average number of bimonthly GFR determinations was 7.6 (minimum 3). Mean starting GFR was 12.4 ml/min.

Serum and urine chemical values were averaged over the entire period of observation in each subject. An average of 6 measurements of 17-OHCS was obtained in each subject.

The data were analyzed by multiple linear regression, using as independent variables in the primary analysis ten tested quantities, mean GFR, age, and the following "dummy variables," i.e., variables scored as 0 or 1: sex, ketoacid therapy, enalapril therapy and each of the four diagnoses listed above. The 35 studies were considered as independent observations for simplicity, even though eight patients were studied twice. Multiple linear regression was carried out using a stepwise technique. First, one-variable model yielding the highest F statistic was computed. Additional variables were added one by one, using a significance level of 0.05 as a criterion for entry. After a variable was added, all variables were re-examined and any were deleted that did not produce an F statistic significant at the 0.05 level.

Two secondary analyses were carried out: first, 17OHCS, urinary urea N, and urinary protein excretion were replaced by the logarithms of these quantities, because their distributions were not normal. Second, 17OHCS was replaced by 17OHCS factored by GFR.

In addition, 17-OHCS was measured in 11 of the 28 patients on 14 occasions when they were changed from essential amino acids to ketoacids (or vice versa) with no change in diet. During six of these comparisons, sufficient GFR determinations to assess progression were not made.

Results of Clinical Tests

When progression rate was examined as a function of all 19 variables, only 17OHCS was a significant regressor, and a linear relationship was shown between rate of change of GFR and 17OHCS excretion. Furthermore, similar linear relationships between progression and 17OHCS were seen in each of three treatment subgroups (see Table 1).

An analysis of variance was performed to compare mean values of each parameter in the three treatment groups, and the results are shown in Table 2. Although mean values for GFR and progression rate differ, these differences failed to attain statistical difference. Serum chemical values also did not differ. 17OHCS differed significantly among the three groups in the order (1) greater than (2) greater than (3). Urinary urea N excretion was the same in the two groups on a severely restricted diet (groups (2) and (3)), but was significantly higher in those on mild protein restriction alone (1). Mean arterial pressure did not differ among the groups.

Since 17OHCS was correlated with GFR, an alternative variable (17OHCS factored by GFR) was employed in the multiple regression analysis in place of 17OHCS. The results set forth in Table 3 show that four regressors are significant at the p less than 0.05 level: serum triglycerides, polycystic kidney disease and 17OHCS/GFR, all of which are associated with more rapid progression, and ketoacid therapy, which is associated with slower progression. The overall correlation coefficient is $r = 0.78$, the same as the previous analysis based on 17OHCS alone.

Changing supplements (from amino acids to ketoacids or vice versa) without change in diet led to significantly (p less than 0.025) lower 17OHCS (but no significant change in 17OHCS/GFR) while on ketoacids than while on amino acids in 13 out of 14 instances (see Table 4). Sequential measurements in one patient whose supplement was changed three times are shown in FIG. 1.

The correlation found above between progression of chronic renal failure and endogenous glucocorticoid production is highly significant statistically. Moreover, ketoacid suppression of glucocorticoid production in patients with chronic renal failure is strongly suggested by these data. Therefore, it is reasonable to conclude that other agents and measures that suppress the production of glucocorticoids should slow or arrest progression of chronic renal failure. Such drugs may either reduce glucocorticoid production directly or reduce receptor binding of the glucocorticoids.

The present invention may be embodied in other specific forms without departing from the spirit or essential attributes thereof and, accordingly, reference should be made to the appended claims, rather than to the foregoing specification as indicating the scope of the invention.

TABLE 1

Correlations between progression rate and 17-hydroxycorticosteroid excretion

| Treatment group | b | r | n | p |
|---|---|---|---|---|
| Mild protein restriction alone | −0.082 | 0.994 | 4 | 0.0005 |
| Essential amino acids | −0.101 | 0.68 | 15 | 0.0052 |
| Ketoacids | −0.102 | 0.76 | 16 | 0.0005 |
| All studies combined | −0.093 | 0.78 | 35 | 0.0001 |

TABLE 2

Comparison of variables by treatment groups

| | Treatment group | | | |
|---|---|---|---|---|
| | (1) Mild protein restriction (n = 4) | (2) Essential amino acids (n = 15) | (3) Keto acids (n = 16) | P |
| GFR, ml/min | 16 | 13 | 8 | n.s. |
| Rate of change of GFR, ml/min/mo | −0.352 | −0.275 | −0.171 | n.s. |
| Serum | | | | |
| calcium × phosphorus, $mg^2/dl^2$ | 39 | 38 | 42 | n.s. |
| alkaline phosphatase, IU/L | 88 | 99 | 105 | n.s. |
| uric acid, mg/dl | 8.1 | 7.2 | 7.8 | n.s. |
| cholesterol, mg/dl | 214 | 211 | 187 | n.s. |
| triglycerides, mg/dl | 205 | 177 | 190 | n.s. |
| 24-hr urinary excretion of: | | | | |
| 17-hydroxycorticosteroids, ug | $5.29^a$ | $4.13^b$ | $3.11^c$ | <0.05 |
| 17-hydroxycorticosteroids/GFR, ratio | 0.36 | 0.40 | 0.52 | n.s. |
| phosphate, mg | 5.58 | 4.27 | 3.42 | n.s. |
| urea N, gm | $9.02^a$ | $5.23^b$ | $5.17^b$ | <0.05 |
| protein, gm | 3.34 | 2.25 | 1.57 | n.s. |
| Mean arterial pressure, mm Hg | 109 | 105 | 105 | n.s. |

$^{a,b}$Means with differing superscripts differ significantly at the p level shown by analysis of variance.

TABLE 3

Multiple regression analysis of factors determining progression rate, using 17OHCS factored by GFR

| Variable | b | partial $r^2$ | model $r^2$ | p |
|---|---|---|---|---|
| Serum triglycerides, mg/dl | −0.0010 | 0.341 | 0.341 | 0.0002 |
| Polycystic kidney disease | −0.1998 | 0.115 | 0.455 | 0.0142 |
| Ketoacid therapy | 0.1489 | 0.086 | 0.541 | 0.0222 |
| 17OHCS/GFR | −0.2123 | 0.059 | 0.600 | 0.0433 |

TABLE 4

Effect of changing from an essential amino acid supplement (AA) to a ketoacid supplement (KA) or vice versa, without change in diet, on urinary 17-hydroxycorticosteroids

| | | Urinary 17-hydroxycorticosteroids ug/day | | |
|---|---|---|---|---|
| Subject | Sequence | On AA | On KA | Difference, AA − KA |
| 3 | AA - KA | 5.47 | 2.68 | 2.79 |
| 4 | AA - KA | 3.65 | 1.75 | 1.90 |
| 4 | KA - AA | 2.48 | 1.75 | 0.73 |
| 4 | AA - KA | 2.48 | 1.98 | 0.50 |
| 6 | AA - KA | 4.40 | 2.90 | 1.50 |
| 6 | KA - AA | 3.40 | 2.90 | 0.50 |
| 9 | AA - KA | 5.25 | 3.65 | 1.60 |
| 10 | AA - KA | 3.30 | 3.18 | 0.12 |
| 11 | KA - AA | 2.40 | 2.20 | 0.20 |
| 18 | AA - KA | 2.90 | 2.17 | 0.73 |
| 19 | AA - KA | 3.15 | 4.35 | −1.20 |
| 22 | AA - KA | 6.77 | 5.60 | 1.17 |
| 25 | AA - KA | 3.30 | 2.43 | 0.87 |
| 26 | AA - KA | 4.13 | 3.74 | 0.39 |
| | | | MEAN | 0.84 |
| | | | S.E.M. | 0.25 |
| | | | p | <0.005 |

I claim:

1. A method of retarding the progression of chronic renal failure in humans comprising administering to the human suffering from chronic renal failure an effective amount of an agent which suppresses the endogenous production of glucocorticoids in said human, said agent not including an agent selected from the group consisting of clonidine, heroin, corticosteroids, and alpha-ketoacid analogs of essential or semi-essential amino acids as the sole effective ingredient.

2. A method according to claim 1, wherein said agent is administered while said human is on a protein-restricted diet.

3. A method according to claim 2, wherein protein is restricted to less than about 0.6 grams of protein daily per kilogram of ideal body weight.

4. A method according to claim 1, wherein said agent is administered while said human is on a phosphorus-restricted diet.

5. A method according to claim 4, wherein phosphorus is restricted to less than about 10 milligrams phosphorus daily per kilogram of ideal body weight.

6. A method according to claim 1, wherein said agent is administered orally.

7. A method according to claim 1, wherein said agent comprises mifepristone.

8. A method according to claim 1, wherein said agent is selected from the group consisting of sodium valproate, enkephalins and their synthetic analogs, opioids excluding heroin, ketoconazole, and oxytocin.

9. A method according to claim 8, wherein said opioid is selected from the group consisting of morphine.

10. A method according to claim 8, wherein said enkephalin analog is DAMME.

* * * * *